United States Patent
Bix

(10) Patent No.: US 9,671,336 B2
(45) Date of Patent: Jun. 6, 2017

(54) ILLUMINATION FOR DETECTING RAINDROPS ON A PANE BY MEANS OF A CAMERA

(71) Applicant: Conti Temic microelectronic GmbH, Nuremberg (DE)

(72) Inventor: Stefan Bix, Baindt (DE)

(73) Assignee: Conti Temic microelectronic GmbH, Nuremberg (DE)

( * ) Notice: Subject to any disclaimer, the term of this patent is extended or adjusted under 35 U.S.C. 154(b) by 0 days.

(21) Appl. No.: 15/102,061

(22) PCT Filed: May 5, 2014

(86) PCT No.: PCT/DE2014/200195
§ 371 (c)(1),
(2) Date: Jun. 6, 2016

(87) PCT Pub. No.: WO2015/081933
PCT Pub. Date: Jun. 11, 2015

(65) Prior Publication Data
US 2016/0305873 A1    Oct. 20, 2016

(30) Foreign Application Priority Data

Dec. 6, 2013   (DE) .................. 10 2013 225 156

(51) Int. Cl.
*G01N 21/55*   (2014.01)
*G01N 21/47*   (2006.01)
(Continued)

(52) U.S. Cl.
CPC ........ *G01N 21/4738* (2013.01); *B60S 1/0844* (2013.01); *G01V 8/12* (2013.01);
(Continued)

(58) Field of Classification Search
CPC ......... G01N 21/4738; G01N 2201/061; G01N 2201/062; G01V 8/12
(Continued)

(56) References Cited

U.S. PATENT DOCUMENTS

| 6,020,704 A | 2/2000 | Buschur |
| 7,253,898 B2 | 8/2007 | Saikalis et al. |

(Continued)

FOREIGN PATENT DOCUMENTS

| DE | 202004015345 | 5/2005 |
| DE | 102006008274 | 8/2007 |

(Continued)

OTHER PUBLICATIONS

International Search Report of the International Searching Authority for International Application PCT/DE2014/200195, mailed Aug. 12, 2014, 2 pages, European Patent Office, HV Rijswijk, Netherlands.
(Continued)

*Primary Examiner* — Tri T Ton
(74) *Attorney, Agent, or Firm* — W. F. Fasse

(57) ABSTRACT

A device for detecting rain on a pane includes a camera (1) and an electrically drivable film (3) that actively emits light (h) as a light sheet (s). The camera and the film are arranged so that the camera can detect an image (i1, i2) of the light sheet that impinges on and is reflected by the pane. The signal detected by the camera correlates with light that has been emitted by the film, and reflected or scattered by the inner face (2.1) or outer face (2.2) of the pane and/or by a raindrop on the outer face of the pane.

9 Claims, 2 Drawing Sheets

(51) Int. Cl.
    *B60S 1/08*     (2006.01)
    *G06K 9/00*     (2006.01)
    *G01V 8/12*     (2006.01)

(52) U.S. Cl.
    CPC ... *G06K 9/00791* (2013.01); *G01N 2201/061* (2013.01); *G01N 2201/062* (2013.01)

(58) Field of Classification Search
    USPC .................................................. 356/445–448
    See application file for complete search history.

(56) References Cited

U.S. PATENT DOCUMENTS

| | | |
|---|---|---|
| 7,259,367 B2 | 8/2007 | Reime |
| 7,855,353 B2 | 12/2010 | Blaesing et al. |
| 8,792,174 B2 | 7/2014 | Schmaelzle et al. |
| 9,120,464 B2 | 9/2015 | Pack et al. |
| 9,335,264 B2 | 5/2016 | Kroekel et al. |
| 2002/0148987 A1 | 10/2002 | Hochstein |
| 2005/0178954 A1 | 8/2005 | Yukawa |
| 2005/0206511 A1 | 9/2005 | Heenan et al. |
| 2006/0076477 A1 | 4/2006 | Ishikawa |
| 2008/0129206 A1* | 6/2008 | Stam ............... B60Q 1/085 315/82 |
| 2010/0208060 A1 | 8/2010 | Kobayashi et al. |
| 2011/0031921 A1 | 2/2011 | Han |
| 2011/0204206 A1 | 8/2011 | Taoka |
| 2011/0273564 A1 | 11/2011 | Seger et al. |
| 2012/0026318 A1 | 2/2012 | Huelsen et al. |
| 2012/0026330 A1 | 2/2012 | Huelsen et al. |
| 2014/0029008 A1* | 1/2014 | Hirai ............... G01N 21/552 356/445 |
| 2015/0034827 A1 | 2/2015 | Kroekel |
| 2015/0276982 A1 | 10/2015 | Kroekel et al. |
| 2015/0321644 A1 | 11/2015 | Kosubek et al. |

FOREIGN PATENT DOCUMENTS

| | | |
|---|---|---|
| DE | 102007050167 | 4/2009 |
| DE | 102010028347 | 11/2011 |
| EP | 1 580 092 | 9/2005 |
| EP | 1 923 695 | 5/2008 |
| JP | 2010-096604 A | 4/2010 |
| JP | 2010-210374 A | 9/2010 |
| JP | 2010-223685 A | 10/2010 |
| WO | WO 2012/092911 | 7/2012 |

OTHER PUBLICATIONS

PCT International Preliminary Report on Patentability including English Translation of PCT Written Opinion of the International Searching Authority for International Application PCT/DE2014/200195, issued Jun. 7, 2016, 5 pages, International Bureau of WIPO, Geneva, Switzerland.

German Search Report for German Patent Application No. 10 2013 225 156.4, dated Dec. 17, 2013, 5 pages, Muenchen, Germany, with English translation, 5 pages.

\* cited by examiner

ILLUMINATION FOR DETECTING RAINDROPS ON A PANE BY MEANS OF A CAMERA

FIELD OF THE INVENTION

The invention relates to a device for detecting rain on a pane by means of illumination and a camera.

BACKGROUND INFORMATION

In U.S. Pat. No. 7,259,367 B2, rain sensing by means of a camera is proposed, said rain sensing providing extensive lighting of the passing-through window of the camera aperture angle with the pane by means of an infrared diode. The camera focus is set to almost infinite and can thus be simultaneously used for driver assistance applications. Due to the imaging on the remote range raindrops are only noticeable as disturbances in the image, which are detected by complex differential measurements of the images recorded with infrared light pulsed or modulated in synchronization with the pixel clock.

A device and a method for detecting rain are described in WO 2012/092911 A1. A camera is disposed behind a pane, in particular in the interior of a vehicle behind a windshield, and focused onto a remote region that lies in front of the pane. A lighting source for generating at least one light beam that is directed at the pane directs the at least one light beam towards the pane such that at least one beam that is reflected from the outer face of the pane impinges on the camera as an external light reflex or external reflex. The light quantity of the at least one beam or light reflex that impinges on the camera can be measured by the camera. One or more light-emitting diodes optionally with a light guide or a light band are indicated as the lighting source. If the aperture angle of the illumination is large enough, the lighting source can also be located inside the camera, e.g. on a circuit board of the camera system.

The sensitivity of the rain detection hereby substantially depends on the configuration of the illumination.

SUMMARY OF THE INVENTION

An object of at least one of the embodiments of this invention is to achieve an optimized illumination for camera-based rain detection, which guarantees high sensitivity.

At least one embodiment of the invention is based on the following basic considerations: the sensitivity of the rain detection depends on the lighting intensity and the area of the detection area on the windshield. An area corresponding to the image of the LEDs reflected on the windshield is covered with LEDs as the lighting source. This covered area is frequently not sufficient for efficient rain detection. The use of a light guide is, in addition, associated with a loss of the light intensity emitted by the lighting source.

A device for detecting rain on a pane according to an embodiment of the invention comprises a camera and an electrically drivable film that actively emits light as a lighting source. The light emitted by the film emerges as a light sheet. The film as a lighting source advantageously generates uniformly flat illumination (light sheet) of an area of the pane, when it is driven electrically in an appropriate manner. The camera and the film are designed and arranged in such a way that the camera can detect a signal from the light or an imaging of the light sheet which is emitted by the film, impinges on the pane and is reflected by the pane. In particular, in this case, the signal detected by the camera or the light sheet(s) correlate(s) with light which is emitted by the film and reflected or scattered at the inner face or outer face of the pane and/or at a raindrop.

The camera preferably comprises an image sensor, for example a CCD or CMOS sensor, and a lens or imaging system for focusing electromagnetic radiation from one or more areas onto the image sensor.

Rain is preferably detected on the outer face of the pane in that the camera is arranged behind the pane and is focused onto a remote region in front of the pane.

An advantage of at least one embodiment of the device according to the invention is that inexpensive lighting is used, which makes it possible to detect rain in a sound and reliable manner. Both the material and the production costs for a device according to the invention are low compared to known camera-based devices with comparably varied areas of application and comparable effectiveness or sensitivity of the rain detection.

The camera and the film that actively emits light are advantageously designed and arranged in such a way that the camera can detect a first mirror image of the light sheet reflected at the inner face of the pane and a second mirror image of the light sheet reflected at the outer face of the pane. In designing the elements of the device, properties of the pane such as e.g. angle of inclination, refractive index and thickness should, in particular, be taken into consideration.

In this case, the camera and the film that actively emits light are preferably designed and arranged in such a way that the first and the second mirror images which can be detected by the camera do not overlap with one another, they can be adjacent to one another in this case. The first mirror image is not dependent on the presence of raindrops in the illuminated area of the pane, whilst the second mirror image is modified or attenuated if raindrops are present in the illuminated area of the pane, as parts of the light intensity are decoupled from the pane by the raindrops and are not reflected to the camera.

According to an advantageous embodiment, the film comprises at least one organic light-emitting diode (OLED) in order to actively emit light. Organic light-emitting diodes are constructed from multiple organic layers. OLEDs thereby comprise organic semiconducting materials, have an anode and a cathode and can be arranged on bendable plastic films. The advantage of OLEDs is that they can be manufactured by printing techniques and, thus, comparatively inexpensively, and they can be electrically driven with direct current voltage. As a consequence, it is possible to limit or adjust the light sheet.

In a preferred embodiment, the film is an electroluminescent film. An electroluminescent film is also designated a capacitor-type luminous film (also abbreviated to luminescent sheet or luminous film), as it resembles a plate capacitor in terms of its construction. The electroluminescent material is located in an electrically insulated form between two electrodes. By applying an electrical alternating voltage to the electrodes, the electroluminescent material is stimulated to emit light. The luminous electroluminescent film is suitable as a lighting source for detecting rain. The advantage of electroluminescent films is that they are thinner and have a less complex construction than OLEDs.

The film advantageously has a plurality of individually electrically drivable areas that emit light. For example, the film can be constructed in the form of a matrix from individually electrically drivable cells that emit light. The form or size of the light sheet can thus be varied or adjusted by being electrically driven in a suitable manner. A film constructed from a plurality of rectangular or frame-shaped cells is advantageous, as a result of which the size of a rectangular illumination area can be varied. This makes it possible to guarantee that the first and the second mirror images, which can be detected by the camera, do not overlap with one another.

The device preferably comprises a lighting control unit in order to electrically drive the film. As a result, an adjusted light sheet can be produced on the film, in particular in the case of a plurality of individually electrically drivable areas or cells that emit light.

The camera is advantageously focused by means of a lens onto a remote region, so that the mirror image(s) of the light sheet is/are shown as (a) blurred image(s) by the camera. As a result, the camera can be used as a multifunctional sensor for one or more additional driver assistance functions which are based on an evaluation of the remote region imaged in a focused manner such as e.g. Lane Departure Warning (LDW), Lane Keeping Assistance/System (LKA/LKS), Traffic Sign Recognition (TSR), Intelligent Headlamp Control (IHC), Forward Collision Warning (FCW), Adaptive Cruise Control (ACC), parking assistance and Emergency Brake Assist (EBA) or Emergency Steering Assist (ESA).

According to a preferred embodiment, the film is arranged in a recess of a housing. The housing can, in particular, be the housing of the camera, the camera electronics or of the lighting control unit. The housing can be produced from metal.

The lighting control unit can advantageously be arranged on a circuit board, wherein the circuit board is an integral part or carrier of the camera electronics. The circuit board can, in addition, be arranged inside the housing.

The camera advantageously comprises a view funnel or a view shield or a lens hood, which particularly restricts the field of vision of the camera (downwards) and ideally minimizes stray and scattered light reflexes. The film is arranged on the view funnel or is integrated into the view funnel. In order to achieve a compact design of the camera with integrated lighting, the film can be integrated into the view funnel in such a way that it "replaces" the view funnel in this area. Alternatively, the view funnel can have an area made of material which is permeable to light and the film can, in particular, be arranged thereon.

BRIEF DESCRIPTION OF THE DRAWINGS

The invention will be explained in more detail below, with reference to figures and embodiment examples, wherein.

DETAILED DESCRIPTION OF EXAMPLE EMBODIMENTS OF THE INVENTION

Figure 1:
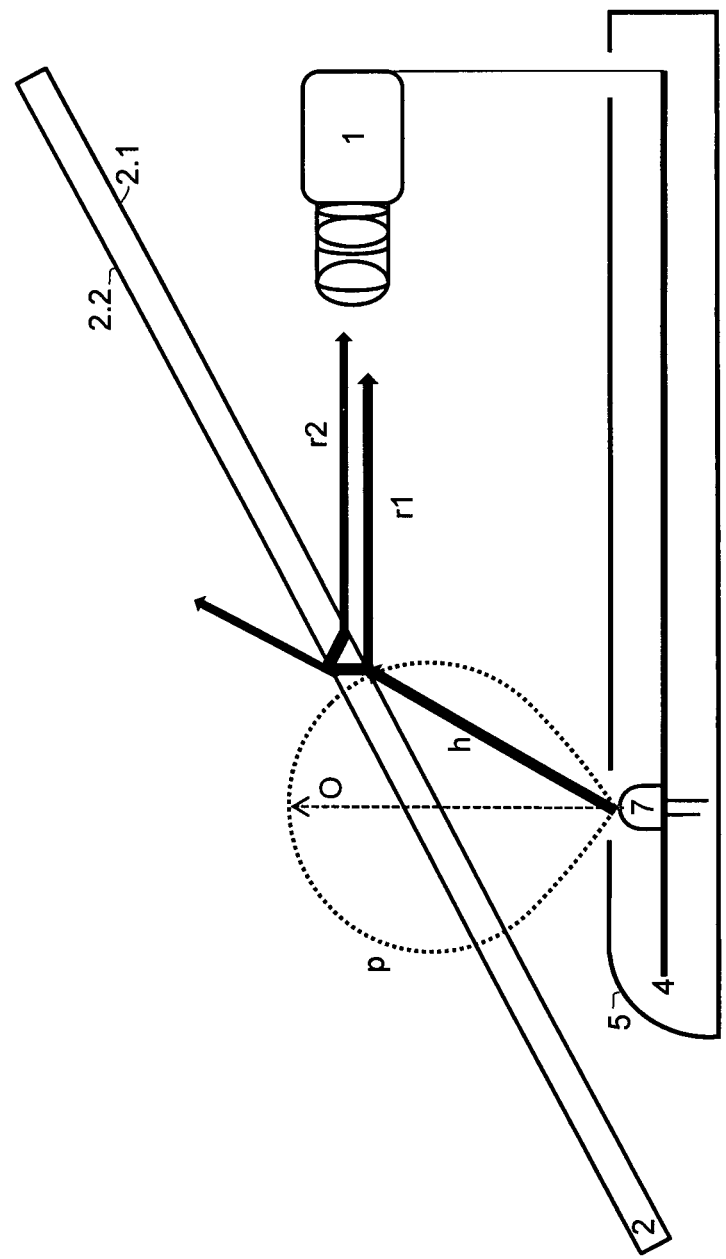
FIG. 1 schematically shows the basic principle of a possible arrangement of the lighting source, pane and camera for detecting rain (longitudinal section)

FIG. 1 shows a longitudinal section of a camera focused on the remote region together with a lens (1) and a LED lighting source (7) which emits light (o, p, h) onto a windshield (2) of a vehicle, which is essentially comparable with an embodiment example of WO 2012/092911 A1. The LED lighting source (7) emits light in a particular distribution (p), in this case with a beam angle or a full width at half maximum (FWHM) of the beam angle distribution of 120° and a maximum intensity in the central beam direction (o). The aperture angle of the lighting is so large that beams reflected from a beam direction (h) at the inner face (2.1) and outer face (2.2) of the pane impinge on the lens or the camera (1) as two spatially separated beams (r1, r2). Most of the light emitted by the LED lighting source (7) (direction o) is, however, not reflected by the windshield (2) to the camera (1) and is lost for rain detection. Due to the focusing on the remote region, the boundary of the beam bundle is only shown as a blurred image by the camera (1). Both reflected beams (r1, r2) are sufficiently separated and their respective light reflexes can be measured with the camera (1).

The portion (r1) of the light beam (h) reflected at the air-pane interface (or inner face of the pane (2.1)) can serve as a reference beam. Of the portion which is transmitted into the pane, that portion is used as a measurement beam (r2) which is reflected at the pane-air/raindrop interface (or outer face of the pane (2.2)) and impinges on the camera (1). Not shown is that portion of the beam which is repeatedly reflected inside the pane (2) (on the pane-air inner face (2.1) after having been reflected at the pane-raindrops outer face (2.2)). The beam paths (h, r1, r2) and light distributions (o, p) are shown schematically.

If, in the event of rain, the outer face (2.2) of the windshield (2) is wetted, the majority of the light transmitted through the inner face (2.1) into the pane is decoupled, so that the reflected portion (r2) is weaker than it is in the case of a dry pane (not shown). The beam (r1) reflected from the inner face (2.1) is unaffected by wetting of the outer face of the pane (2.2).

By comparing the measured light reflexes of both beams (r1 to r2), the reduced signal in the event of rain can therefore be easily measured and a windshield wiper can be activated accordingly.

The LED lighting source (7) preferably comprises a plurality of LEDs having a wide beam angle which are arranged in a row, only one of which is shown in FIG. 1. The additional LEDs can, in particular, be arranged in a row perpendicular to the plane shown in FIG. 1. A plurality of LEDs is advantageous, in order to achieve sufficient illumination for detecting rain. The LEDs are, in particular, arranged as upwardly beaming SMD components on a circuit board (4). The circuit board (4) can advantageously be a printed circuit board (PCB) of the camera electronics, which is arranged inside a housing (5) in order to protect it against dirt, humidity and electromagnetic disturbances. The connecting line between the camera (1) and the circuit board (4) in FIG. 1 is only intended to illustrate the fact that the circuit board (5) is an integral part of the camera electronics.

The area of the windshield (2) illuminated by the LEDs (7), which can be used to detect rain, is very small, e.g. of the order of a few $mm^2$. Raindrops, which are located on the outer face of the pane, are only illuminated by LEDs in this (detection) area. The sensitivity of the rain detection depends on the light intensity and the size of the detection area on the windshield. With LEDs as a lighting source (7), the detection area corresponds to the mirror image which is generated by reflection of the LED emission surfaces at the pane. The (detection) area covered as a result is not sufficient for effective rain detection.

Figure 2:
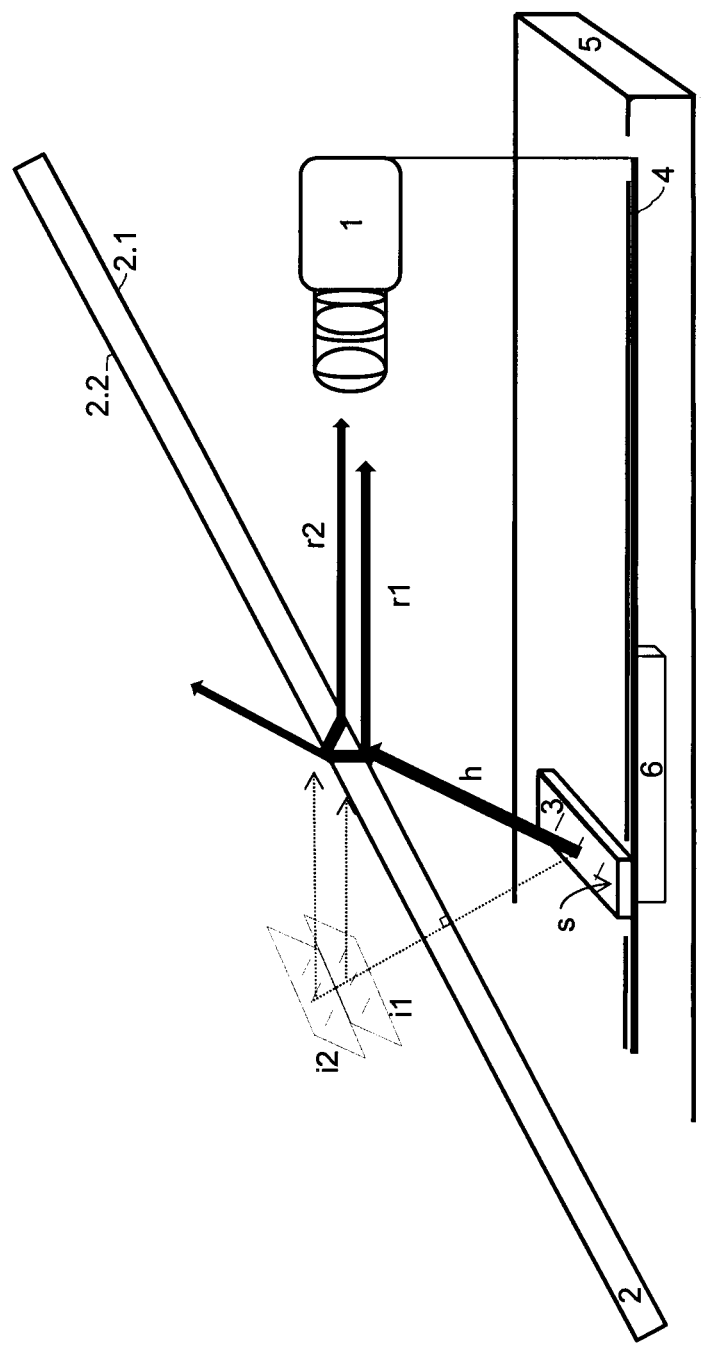
FIG. 2 shows an arrangement of a film that actively emits light, pane and camera for improved rain detection.

FIG. 2 shows an arrangement with a film (3) that actively emits light as the lighting source. The film is electrically drivable and can, in particular, comprise one or more organic light-emitting diodes (OLEDs). The OLED film (3) lights up when it is driven with a suitable direct voltage by a lighting control unit (6). The light (h) emitted by the OLED film (3) results in a uniformly illuminated film surface (s) (light sheet).

The mirror images or virtual images of the light sheet (s) produced by the inner face (i1) or outer face (i2) of the pane are visible to the camera (1).

Depending on the size of the illuminated area (s), the nature (refractive index and thickness) of the windshield, the angles between the illuminated area (s) and the windshield (2) as well as between the windshield (2) and the optical axis of the camera (1), overlapping of the first (i1) and second (i2) mirror images can occur in the camera image. This overlapping area cannot be used or can only be used with difficulty for effectively detecting rain. An overlapping of the first (i1) and second (i2) mirror images in the camera image should preferably be avoided.

Adjusting the light sheet (s) represents one possible measure for avoiding this overlapping. This is possible, if the film (3) has a plurality of individually electrically drivable areas that emit light (h). To this end, the film (3) can be constructed in the form of a matrix from individually electrically drivable cells that emit light (h). By electrically driving the individual cells by means of the lighting control unit (6), the form or size of the light sheet (s) can be adjusted. As a result, the light sheet can therefore be limited in such a manner that there is no such overlapping.

In order to adapt the device for various vehicles having various angles of inclination of the windshield (2), the film (3) can be arranged at a predefined, fixed angle and optionally also at a fixed, predefined distance from the respective windshield (2). To this end, the film (3) can, in particular, be arranged in such a way that it is impinged on at a corresponding tilting angle. A curved arrangement of the film (3) is also possible, as a result of which minor differences of the angle of inclination can be sufficiently compensated for in windshields (2). As a result, the covering or illumination of a similar detection area on the respective windshield (2) is possible for different windshield inclinations in different types of vehicles.

LIST OF REFERENCE NUMERALS

1 Camera
2 Windshield
2.1 Inner face of the windshield
2.2 Outer face of the windshield
3 Film that actively emits light as a lighting source
4 Circuit board
5 Housing
6 Lighting control unit
7 LED lighting source
p Distribution of the light emitted by the lighting source
o Emission direction with the maximum intensity of the lighting source
h Lighting beam direction which is detected by the camera
r1 Portion of h, which is reflected at the inner face of the pane and detected by the camera
r2 Portion of h, which is reflected at the outer face of the pane and detected by the camera
s Light sheet
i1 Mirror image of the light sheet reflected at the inner face of the pane
i2 Mirror image of the light sheet reflected at the outer face of the pane

The invention claimed is:

1. A device for detecting rain on a pane, comprising
a camera, and
an electrically drivable film that actively emits light,
wherein the light emitted by the film emerges as a light sheet, and
wherein the camera and the film are configured and arranged so that the camera can detect a signal from the light which is emitted by the film, impinges on the pane and is reflected by the pane, wherein the camera can detect a first mirror image of the light sheet reflected at an inner face of the pane and a second mirror image of the light sheet reflected at an outer face of the pane.

2. The device according to claim 1, wherein the first mirror image and the second mirror image which can be detected by the camera do not overlap with one another.

3. The device according to claim 1, wherein the film comprises an organic light-emitting diode.

4. The device according to claim 1, wherein the film is an electroluminescent film.

5. The device according to claim 1, wherein the film has a plurality of individually electrically drivable areas that emit light.

6. The device according to claim 1, further comprising a lighting control unit configured and arranged to electrically drive the film.

7. The device according to claim 1, further comprising a lens, wherein the camera is focused by the lens onto a remote region, so that the mirror images of the light sheet are shown as blurred images by the camera.

8. The device according to claim 1, further comprising a housing, wherein the film is arranged in a recess of the housing.

9. The device according to claim 1, wherein the camera includes a view funnel and the film is arranged on the view funnel or is integrated into the view funnel.

* * * * *